United States Patent [19]
Chopin et al.

[11] Patent Number: 5,888,291
[45] Date of Patent: Mar. 30, 1999

[54] ALKALINE-EARTH METAL-, COPPER- AND OPTIONALLY TITANIUM-BASED SILICATES, BLUE OR VIOLET PIGMENTS BASED ON THESE SILICATES, PROCESS FOR THEIR PREPARATION AND THEIR USE

[75] Inventors: Thierry Chopin, Saint-Leu-la-Forêt; Pierre Macaudiere, Asnières-sur-Seine, both of France

[73] Assignee: Rhone-Poulenc Chimie, Courbevoie Cedex, France

[21] Appl. No.: 693,238

[22] PCT Filed: Feb. 6, 1995

[86] PCT No.: PCT/FR95/00140

§ 371 Date: Nov. 7, 1996

§ 102(e) Date: Nov. 7, 1996

[87] PCT Pub. No.: WO95/21791

PCT Pub. Date: Aug. 17, 1995

[30] Foreign Application Priority Data

Feb. 11, 1994 [FR] France .................. 94 01560

[51] Int. Cl.$^6$ ...................................... C09C 1/02
[52] U.S. Cl. ................ 106/466; 106/444; 106/461
[58] Field of Search ................ 106/495, 497, 106/498, 444, 461, 466, 470; 423/331

[56] References Cited

U.S. PATENT DOCUMENTS 4,698,449  10/1987  Imai et al. ................ 585/469
5,228,910  7/1993  Joyce et al. ................ 106/450

OTHER PUBLICATIONS

JP, A, 56115360, Okumura, Abstract, Sep. 1981.

SU, A, 1623951, Abstract, Jan. 1991.

Fitzhugh et al, "A Purple Barium, Copper Silicate Pigment From China", Chem. Abstracts Col. 177, No. 25, Dec. 1992.

Bayer et al, "Thermoanalytical Study Of The Formation and Decomposition Of Alkaline Earth Copper Silicates", Chem. Abstracts, vo. 86, No. 10, Mar. 1977.

*Primary Examiner*—Deborah Jones
*Attorney, Agent, or Firm*—Burns, Doane, Swecker & Mathis, L.L.P.

[57] ABSTRACT

Alkaline-earth metal- and copper- and optionally titanium-based silicates in the form of agglomerates consisting either of monocrystalline grains or of aggregates themselves consisting of monocrystalline particles.

These silicates are prepared by a process including the following stages: a silica sol or a silicate and optionally a titanium sol is mixed with salts of the other constituent elements of the silicate with the exception of oxygen; the mixture thus obtained is dried, preferably by spraying, and the product obtained is calcined. The silicates may be employed as colored pigments in plastics, paints, varnishes, rubbers, ceramics, glazes, papers, inks, cosmetic products, dyes and laminated coatings.

27 Claims, No Drawings

ALKALINE-EARTH METAL-, COPPER- AND OPTIONALLY TITANIUM-BASED SILICATES, BLUE OR VIOLET PIGMENTS BASED ON THESE SILICATES, PROCESS FOR THEIR PREPARATION AND THEIR USE

FIELD OF THE INVENTION

The present invention relates to alkaline-earth metal-, copper- and optionally titanium-based silicates, to blue or violet pigments based on these silicates, to a process for their preparation and to their use.

BACKGROUND

Inorganic coloring pigments are already widely employed in many industries, especially in those of paints, plastics and ceramics. In such applications, the properties consisting, inter alia, of thermal and/or chemical stability, dispersibility (ability of the product to disperse correctly in a given medium), intrinsic color, coloring power and hiding power constitute some particularly important criteria to be taken into consideration in the choice of a suitable pigment.

Unfortunately the problem is that most of the inorganic pigments which are suitable for applications such as the above and which are actually employed nowadays on an industrial scale generally rely on metals (especially cadmium, lead, chromium and cobalt) the use of which is becoming increasingly strictly regulated, or even prohibited, by the legislations of many countries, bearing in mind, in fact, their toxicity, which is reputed to be very high. It is thus possible to mention more particularly, by way of nonlimiting examples, the case of red pigments based on cadmium selenide and/or cadmium sulphoselenide and for which substitutes based on rare-earth sulphides are now already proposed, and that of green pigments which, for their part, exhibit the disadvantage of containing, in most cases, chromium especially in the form of cobalt chromite, of Victoria Green (chromium-based garnets) or of chromium(III) oxide. The case of cobalt-based blue pigments may also be mentioned.

It can be seen, therefore, that the search for, the development and finally the provision of new substitute inorganic pigments nowadays constitute one of the most important economic and industrial objectives.

Barium and copper silicates, especially of blue or violet color, are furthermore known, but the preparation of these products presents difficulties. In fact, these silicates are generally obtained by grog firing. In this case, because of the high temperatures required by this type of process, melt phases are necessarily involved as intermediates and, as a result, products are obtained essentially in the form of glasses. These glasses exhibit a very dark violet color and their use as colorants is very limited. At the most, in fact, they can be employed for coloring ceramics or fruits because it is difficult to grind them to a particle size of less than about ten microns, a particle size which is necessary for coloring other materials, because such grinding generally entails an excessive change in color, which makes them unusable.

There is therefore an undoubted need for colored pigments based on alkaline-earth metal and copper silicates, of fine particle size, permitting the coloring of a wide range of materials and also exhibiting a wide range of colors, especially in the blue and the violet.

SUMMARY OF THE INVENTION

A first objective of the invention is to offer a pigment of this type.

A second objective of the invention is the development of a process for the preparation of a pigment of this type.

To this end, the silicate according to the invention, based on alkaline-earth metal and copper or alkaline-earth metal, titanium and copper is characterized in that it is in the form of agglomerates consisting monocrystalline or predominantly monocrystalline grains or of aggregates, themselves consisting of monocrystalline particles.

The invention also relates to phase-pure silicates which correspond to the formula $BaCuSi_2O_6$ or the formula $BaCuSi_4O_{10}$.

The invention also covers colored pigments, especially of blue or violet color, based on at least one silicate of the abovementioned type.

Furthermore, the process for the preparation of a silicate according to the invention is characterized in that it comprises the following stages:

a silica sol or a silicate and optionally a titanium sol is mixed with salts of other constituent elements of the silicate with the exception of oxygen;

the mixture thus obtained is dried;

the product obtained is calcined.

Other characteristics, details and advantages of the invention will become clearer on reading the description and the concrete but nonlimiting examples which are to follow.

DETAILED DESCRIPTION OF THE INVENTION

According to a first embodiment the present invention relates to silicates based on an alkaline-earth metal and copper.

According to a second embodiment the silicates of the invention are based on an alkaline-earth metal, titanium and copper.

Here, and in the remainder of the description alkaline-earth metal-based is intended to mean based on at least one alkaline-earth element, it being possible, in fact, for a silicate of the invention to include a number of alkaline-earth elements in its formula.

In both cases the alkaline-earth metal may be more particularly barium. It may also be calcium.

The alkaline-earth element may also be partially substituted by a rare earth.

A rare earth is here intended to mean the elements of the group consisting of yttrium and the elements of the Periodic Classification of atomic number between 57 and 71 inclusive. The Periodic Classification of the elements to which reference is made is that published in the Supplement to the Bulletin de la Société Chimique de France no. 1 (January 1966).

According to a preferred embodiment of the invention a light rare earth is employed; a light rare earth is intended to mean lanthanum, cerium, praseodymium and neodymium. Lanthanum may be mentioned very particularly.

The copper may also be partially replaced. The substituting element may be an alkali metal, especially sodium or lithium. It may also be zinc, nickel, cobalt and manganese.

It is possible within the scope of the present invention to have a substitution both on the alkaline-earth metal and copper.

The silicates of the invention may correspond to the formula $MCuSi_2O_6$ or $MCuSi_4O_{10}$ or else $MCuTiSi_3O_9$, M denoting the alkaline-earth metal and it being possible for M and Cu to be substituted. These formulae are given by way of example and must not be interpreted as implying limitations.

The silicates of the invention are characterized by their constitution. As indicated above, they are in the form of agglomerates consisting either of monocrystalline or predominantly monocrystalline grains or of aggregates, themselves consisting of monocrystalline particles.

The agglomerates may be of variable size. Their average size is usually not more than 20 $\mu$m, preferably not more than 10 $\mu$m. This size is determined by CILAS particle size measurement. The monocrystalline or predominantly monocrystalline grains and the aggregates usually have an average size which varies between 1 and 3 $\mu$m. The monocrystalline particles which form the aggregates have themselves an average size which may vary between a few angstroms and some tens of nanometres.

The silicates of the invention are additionally preferably in the form of a powder.

An advantageous property of the silicates of the invention lies in the fact that they can be deagglomerated. This means that the size of the agglomerates can be very easily reduced by milling in mild conditions, that is to say, for example, by using a mill of the air jet type. This deagglomeration, which makes it possible to reach the grains or the aggregates of which the agglomerates consist does not alter the color of the products in an unacceptable manner.

Thus, the silicates of the invention obtained directly by the process which will be described later exhibit, after deagglomeration, a particle size close to the average size of the grains or of the aggregates, that is to say not more than 5 $\mu$m and more particularly not more than 3 $\mu$m.

According to a particular embodiment of the invention, the silicates of the invention, besides their fineness, also have a narrow particle size distribution. Thus, in the case of a product which is deagglomerated or otherwise, their dispersion index may be not more than 1 and more particularly not more than 0.7. This dispersion index is that given by the ratio $(\phi_{84}-\phi_{16})/2\phi_{50}$, in which $\phi_{84}$, $\phi_{16}$ and $\phi_{50}$ denote the diameters of the particles corresponding to 84%, 16% and 50% of the latter.

The silicates of the invention furthermore exhibit a wide range of colors. More precisely, they can exhibit the following chromaticity coordinates:

L* of between 25 and 80; a* between −15 and +35; b* between −5 and −55.

The chromaticity coordinates L*, a* and b* are given here and for the remainder of the description in the CIE 1976 (L*, a*, b*) system as defined by the International Commission on Illumination and listed in the Collection of French Standards (AFNOR), calorimetric color no. X08-12 (1983). They are determined by means of a calorimeter marketed by the Pacific Scientific Company. The nature of the illuminant is D65. The surface observed is a circular disc 12.5 cm$^2$ in area. The observing conditions correspond to viewing at an angle of opening of 10°. In the measurements which are given the specular component is excluded.

L* gives a measurement of the reflectance (light/dark shade) and thus varies from 100 (white) to 0 (black).

a* and b* are the values of the color tendencies:

positive a*=red negative a*=green positive b*=yellow negative b*=blue

L* therefore represents the change from black to white, a* the change from green to red and b* the change from yellow to blue.

More particular silicates according to the invention will now be described.

One of these silicates corresponds to the formula (1) $BaCuSi_2O_6$ and has the following chromaticity coordinates:

L*>30; a*>15; b*<−30.

The invention makes it possible to obtain more particularly a nondeagglomerated silicate of formula (1) exhibiting the following chromaticity coordinates:

L*=44; a*=29; b*=−50.

Another of these silicates corresponds to the formula (2) $BaCuSi_4O_{10}$ and has the following chromaticity coordinates:

L*>40; a*<0; b*<−30.

The invention makes it possible to obtain more particularly a nondeagglomerated silicate of formula (2) exhibiting the following chromaticity coordinates:

L*=57; a*=−2.5; b*=−33.

In addition, the products of formula (1) and (2) are phase-pure. Phase-pure is here intended to mean products whose X-ray spectra make it possible to detect only the existence of a single phase in routine analysis conditions.

The process for the preparation of the products of the invention will now be described.

This process comprises a first stage in which a silica sol or a silicate is mixed with salts of the other constituent elements of the silicate with the exception of oxygen. If appropriate, a titanium sol is also employed for the preparation of a silicate including titanium.

The term sol is here employed within the most common meaning as denoting any system consisting of solid fine particles of colloidal size in suspension in a generally aqueous liquid phase.

The silica sol employed may be one of those consisting of elementary particles of 100 to 500 Å.

The titanium sol employed may be one of the sols exhibiting, for example, a pH of between 0.8 and 2.5 and consisting of elementary $TiO_2$ crystallites between 10 and 100 Å in size, agglomerated into submicron accretions from 200 to 1000 Å in size.

As silicate there may be mentioned organic silicates such as ethyl silicate and quaternary ammonium silicates such as tetramethylammonium, tetraethylammonium, tetrapropylammonium or tetrahydroxyethylammonium silicate.

Salts of the constituent elements of the silicate other than oxygen are furthermore employed. Any type of salt may be employed insofar as it is soluble in the reaction mixture and especially in the liquid phase of the sol.

Salts of inorganic acids such as nitrates, chlorides or sulphates are generally employed. It is preferred to employ nitrates.

It is optionally possible to employ salts of organic acids; in this case the latter are chosen more particularly from the salts of saturated aliphatic carboxylic acids or from the salts of hydroxycarboxylic acids. Formates, acetates, propionates and citrates may be mentioned by way of example.

The mixing of the sol(s) and of the salts may be done in any order, for example by introducing the sol into the solution containing the salts or vice versa, it being possible for the order of introduction to depend on the stability of the sol as a function of pH. The work is usually done at ambient temperature, but it is possible to heat the mixture.

The mixture thus obtained is then dried.

The drying may be carried out by any known means, for example in an oven.

However, according to a preferred embodiment of the invention the drying is carried out by spraying, that is to say by spraying the mixture into a hot atmosphere (spray drying). This type of drying makes it possible to obtain products with a fine and narrow particle size distribution.

The spraying may be carried out by means of any sprayer known per se, for example a spraying nozzle of the watering rose or other type. It is also possible to employ so-called turbine sprayers. Concerning the various spraying techniques capable of being used in the present process reference may be made especially to the fundamental work by Masters entitled "Spray-Drying" (second edition, 1976, George Godwin Publishers—London).

By way of example, the temperature at the beginning of drying of the gases is usually between 200 and 300° C.; that at the exit may vary between 110 and 200° C. The pressure may be, for example, between 2 and 3 bars.

It will be noted that it is also possible to apply the spray-drying operation by means of a "flash" reactor, for example of the type developed by the Applicant Company and described especially in French Patent Applications nos. 2 257 326, 2 419 754 and 2 431 321. In this case, the processing gases (hot gases) are driven in a helical motion and flow into a vortex sink. The mixture to be dried is injected along a trajectory coinciding with the axis of symmetry of the helical trajectories of the gases, and this enables the quantity of motion of the gases to be transferred completely to the mixture to be treated. The gases thus actually fulfil a two-fold function; on the one hand spraying, that is to say the conversion of the initial mixture into fine droplets and, on the other hand, drying of the droplets obtained. Moreover, the extremely short residence time (generally shorter than approximately $1/10$ of a second) of the particles in the reactor offers the advantage, inter alia, of limiting possible risks of overheating as a result of an excessively long contact with the hot gases.

Depending on the respective flow rates of the gases and of the mixture to be dried, the entry temperature of the gases is between 400° to 900° C. and more particularly between 600° and 800° C.; the temperature of the dried solid between 150° and 300° C.

Insofar as the flash reactor mentioned above is concerned, reference may be made in particular to FIG. 1 of French Patent Application 2 431 321.

This reactor consists of a combustion chamber and of a contact chamber made up of a double cone or of a truncated cone whose upper part diverges. The combustion chamber opens into the contact chamber via a narrow passage.

The upper part of the combustion chamber is provided with an opening allowing the fuel phase to be introduced.

On the other hand, the combustion chamber includes a coaxial internal cylinder, thus defining inside it a central zone and an annular peripheral zone which has perforations situated mostly towards the upper part of the apparatus. The chamber includes at least six perforations distributed on at least one circle, but preferably on a number of axially spaced circles. The total area of the perforations located in the lower part of the chamber may be very small, of the order of $1/10$ to $1/100$ of the total area of the perforations of the coaxial internal cylinder.

The perforations are usually circular and have a very small thickness. The ratio of their diameter to the thickness of the wall is preferably at least 5, the minimum thickness of the wall being limited only by essential mechanical requirements.

Finally, an elbow-shaped pipe opens into the narrow passage, whose end opens into the axis of the central zone.

The gas phase driven with a helical motion (called helical phase in what follows) is made up of a gas, generally air, introduced into an orifice made in the annular zone; this orifice is preferably situated in the lower part of the zone.

In order to obtain a helical phase at the narrow passage, the gas phase is preferably introduced at low pressure into the abovementioned orifice, that is to say at a pressure below 1 bar and more particularly at a pressure of between 0.2 and 0.5 bars above the pressure existing in the contact chamber. The velocity of this helical phase is generally between 10 and 100 m/s and preferably between 30 and 60 m/s.

Furthermore, a fuel phase which may be especially methane is injected axially via the abovementioned opening into the central zone at a velocity of approximately 100 to 150 m/s.

The fuel phase is ignited by any known means in the region where the fuel and the helical phase are in contact.

Subsequently, the imposed flow of the gases in the narrow passage takes place according to a set of trajectories coinciding with sets of generatrices of a hyperboloid. These generatrices are based on a set of circles, of small-sized rings located near and below the narrow passage, before diverging in all directions.

The mixture to be treated is next introduced in the form of liquid via the abovementioned pipe. The liquid is then broken up into a multitude of drops, each of them being conveyed by a volume of gas and subjected to a motion creating a centrifugal action. The flow rate of the liquid is usually between 0.03 and 10 m/s.

The ratio of the quantity of the natural motion of the helical phase to that of the liquid mixture must be high. In particular it is at least 100 and preferably between 1000 and 10,000. The quantities of motion at the narrow passage are calculated as a function of the entry flow rates of the gas and of the mixture to be treated, and of the section of the passage. An increase in the flow rates produces an enlargement in the size of the drops.

In these conditions the natural motion of the gases is imposed in its direction and its intensity onto the drops of the mixture to be treated, which are separated from one another in the region of convergence of the two streams. The velocity of the liquid mixture is furthermore reduced to the minimum needed to obtain a continuous stream.

At the end of the drying stage the product obtained, which is a precursor of the silicate of the invention, is calcined.

The calcination temperature varies between the temperature needed to form the silicate phase and that above which a glass is formed. This temperature therefore varies as a function of the type of silicate prepared, and is usually between 900° and 1100° C. This calcination is generally carried out in air; however, calcination under inert gas is not ruled out.

At the end of the calcination, products exhibiting a wide range of colors which can vary from blue to violet are obtained.

Furthermore, especially in the case of spray-drying, the particle size of the recovered product is fine and uniform and is generally not more than 20 microns, preferably not more than 10 microns. This is the particle size of the agglomerates. However, it is quite possible to reduce this particle size merely by deagglomeration. Products are thus obtained which, as indicated above, have a particle size of not more than 5 $\mu$m and more particularly not more than 3 $\mu$m.

The silicates of the invention may be employed as pigments as they are, or may form part of the composition of colored, especially blue or violet, pigments.

The silicates or pigments according to the invention have a very good coloring power and a very good hiding power and, consequently, are suitable for coloring many materials such as plastics, paints and ceramics. In this respect the wide applicability of the silicates or pigments according to the invention constitutes one of their great merits.

Thus, and still more precisely, they may be employed in the coloring of plastics, which may be of the thermoplastic or thermosetting type.

As thermoplastic resins capable of being colored according to the invention there may be mentioned, purely by way of illustration, polyvinyl chloride, polyvinyl alcohol, polystyrene, styrene-butadiene, styrene-acrylonitrile and acrylonitrile-butadiene-styrene (ABS) copolymers, acrylic polymers, especially polymethyl methacrylate, polyolefins such as polyethylene, polypropylene, polybutene and polymethylpentene, cellulose derivatives such as, for example, cellulose acetate, cellulose acetobutyrate, ethyl cellulose and polyamides including polyamide 6—6.

With regard to the thermosetting resins for which the silicates or pigments according to the invention are also suitable, there may be mentioned, for example, phenolic plastics, amino plastics, especially urea-formaldehyde and melamine-formaldehyde copolymers, epoxy resins and thermosetting polyesters.

The silicates or pigments of the invention may also be applied in special polymers such as fluoro-polymers, in particular polytetrafluoroethylene (PTFE), polycarbonates, silicone elastomers and polyimides.

In this specific application for coloring plastics the silicates or pigments of the invention may be employed directly in the form of powders. It is also possible, preferably, to use them in a predispersed form, for example as a premix with a part of the resin or in the form of a paste concentrate or of a liquid, and this allows them to be introduced at any stage of manufacture of the resin. This latter point constitutes a particularly great advantage of the silicates or pigments according to the invention.

Thus, the silicates or pigments according to the invention may be incorporated in plastics such as those mentioned above in a proportion by weight generally ranging either from 0.01 to 5% (based on the final product) or from 40 to 70% in the case of a concentrate.

The silicates or pigments of the invention may also be employed in the field of paints and varnishes and more particularly in the following resins: alkyd resins, among which the one most widely used is called glycerophthalic, long- or short-oil-modified resins, acrylic resins derived from esters (methyl or ethyl) of acrylic and methacrylic acid, optionally copolymerized with ethyl, 2-ethylhexyl or butyl acrylate, vinyl resins such as, for example, polyvinyl acetate, polyvinyl chloride, polyvinylbutyral, polyvinylformal and copolymers of vinyl chloride and vinyl acetate or vinylidine chloride, amino plastic or phenolic resins, in most cases modified ones, polyester resins, polyurethane resins, epoxy resins and silicone resins.

The silicates or pigments are generally used in a proportion of 5 to 30% by weight of the paint and of 0.1 to 5% by weight of the varnish.

The silicates or pigments of the invention are also suitable for coloring ceramics such as, for example, porcelains, crockery and stoneware, this being either by coloring the ceramic throughout (physical mixing of the ceramic powder and the pigment) or by coloring only the surface of the latter by means of glazes (glass coating compositions) containing the pigment.

In this application the quantity of silicates or pigments used is generally between 1 and 30% by weight relative either to the whole of the ceramic or relative to the glaze alone.

Finally, the silicates or pigments according to the invention are also capable of being suitable for applications in the rubber industry, especially in floor coverings, in the paper industry and in printing inks, in the field of cosmetics and in many other uses such as, for example, and without any limitation being implied, dyeing and finishing of leather and laminated coatings for kitchens and other work surfaces.

Where cosmetics are more particularly concerned, the products of the invention may be employed in the preparation of make-up compositions and especially the preparation of eye shadows and blushers. These make-ups may take the form of dry make-ups or fatty make-ups. The pigment content in such make-ups may vary within wide limits, for example between 2 and 20% by weight. The dry make-ups are powders based, for example, on talc, magnesium carbonate, zinc stearate, zinc oxide, kaolin and magnesium alurminium silicate, which are filled with pigment and agglomerated either with methyl cellulose or with stearates. The products of the invention may also form part of the composition of make-up crayons.

Finally, the present invention covers colored compositions of matter, especially of the plastics, paints, varnishes, rubbers, ceramics, glazes, papers, inks, cosmetic products, dyes and laminated coatings type, which include colored silicates or pigments according to the invention.

Examples will now be given.

EXAMPLE 1

This example illustrates the preparation of $BaCuSi_4O_{10}$.

32.66 g of barium nitrate [$(Ba(NO_3)_2$; M=261.35] and 30.2 g of copper nitrate [$Cu(NO_3)_2$ $3H_2O$, M=241.60] are mixed in 400 ml of purified water.

The mixture is heated to about 60° C. 75 g of silica sol (Ludox containing 40% of $SiO_2$) are added.

The mixture is sprayed in a Buchi sprayer.

Spraying conditions: flow rate 600 ml/h gas entry temperature: 245° C.

gas exit temperature: 128° C.

The dried product is then calcined.

Calcination conditions: 3 hours at 1050° C. (300° C./h)

The blue-colored powder obtained has the following characteristics:

X-ray pattern: $BaCuSi_4O_{10}$ color: $L^*$=57

$a^*$=−2.5

$b^*$=−33 diameter $\phi_{50}$=7.9 $\mu$m, reduced to less than 2 $\mu$m merely by deagglomeration with an air jet.

EXAMPLE 2

This example illustrates the preparation of a silicate of the type of Example 1 but doped with lanthanum and with sodium and of the formula $Ba_{0.5}La_{0.5}Cu_{0.5}Na_{0.5}Si_4O_{10}$.

32.66 g of barium nitrate, 43.7 ml of a 2.86M solution of lanthanum nitrate (d=1.7, that is 74.3 g), 30.2 g of copper nitrate and 10.6 g of sodium nitrate are mixed in 400 ml of purified water.

The mixture is heated to about 60° C. with stirring and 60 g of $SiO_2$ (150 g of Ludox sol containing 40% of $SiO_2$) are then added.

The mixture is sprayed in a Buchi sprayer.

Spraying conditions: flow rate 700 ml/h entry temperature: 240° C.

exit temperature: 115° C.

The product is then calcined.

Calcination conditions: 2 hours at 950° C.

The blue-colored powder obtained has the following characteristics:

X-ray pattern: mixture of phases $La_2Si_2O_7$ $BaCuSi_4O_{10}$
crystobalite $SiO_2$ (trace)
color: L*=58
 a*=5
 b*=−43
$\phi_{50}$ diameter=10 μm, reduced to 2–3 μm merely by deagglomeration with an air jet.

EXAMPLE 3

This example illustrates the preparation of $BaCuSi_2O_6$.

32.66 g of barium nitrate [$Ba(NO_3)_2$ $3H_2O$, M=241.60] are mixed in 300 ml of purified water.

The mixture is heated to about 60° C. 37.5 g of $SiO_2$ sol (Ludox containing 40% of $SiO_2$) are added.

The mixture is sprayed in a Buchi sprayer.
Spraying conditions: solution flow rate 800 ml/h
entry temperature: 240° C.
exit temperature: 120° C.
The product obtained is calcined.
Calcination conditions: 2 hours at 950° C. (300° C./h)
The violet-colored powder obtained has the following characteristics:
X-ray pattern: tetragonal $BaCuSi_2O_6$
color: L=44
 a=29
 b=−50
$\phi_{50}$ diameter: 5.8 μm, σ/m=0.9 (dispersion index).
after air jet milling
color: L*=48
 a*=25
 b*=−45
$\phi_{50}$ diameter: 1.75 μm, σ/m=0.7 (dispersion index).

EXAMPLE 4

A silicate of formula $Ba0.75Ca_{0.25}CuSi_2O_6$ is prepared by following the procedure of Example 3 and by introducing the reactants in stoichiometric quantity. The calcium is introduced in the form of nitrate.

The unmilled product obtained has an average diameter of less than 3 μm and has a violet blue color. Its chromaticity coordinates are the following:
L*=57.9
a*=5.4
b*=−32.6

EXAMPLE 5

A silicate of formula $BaCu_{0.5}Zn_{0.5}Si_2O_6$ is prepared by following the procedure of Example 3 and by introducing the reactants in stoichiometric quantity. The zinc is introduced in the form of nitrate.

The unmilled product obtained has an average diameter of 2.4 μm and has a violet blue color. Its chromaticity coordinates are the following:
L*=66.3
a*=12.1
b*=−32.5

EXAMPLE 6

This example illustrates the preparation of the silicate of formula $Ba_{0.9}Cu_{0.1}TiSi_3O_9$.

29.4 g of barium nitrate, 3.02 g of copper nitrate and 49.3 g of titanium sol containing 20.26% of $TiO_2$ are dissolved in 350 ml of water at about 60° C.

56.25 g of silica sol containing 40% $SiO_2$ are added and the mixture is sprayed in a Buchi sprayer.
Spraying conditions: entry temperature: 239° C.
exit temperature: 122° C.
solution flow rate: 800 ml/h.
The powder obtained is calcined for 2 hours at 1000° C.
A violet-colored powder is obtained.
Color: L*=76
 a*=12
 b*=−20
$\phi_{50}$ diameter=4.7 μm, σ/m=0.56. The average diameter can be easily reduced to less than 2 μm merely by deagglomeration with an air jet.

EXAMPLE 7

This example illustrates the preparation of a silicate of formula $Ba_{0.5}Nd_{0.5}Cu_{0.5}Na_{0.5}Si_2O_6$.

32.66 g of barium nitrate, that is 0.125 moles of Ba; 84.6 g of a neodymium nitrate solution containing 21.3% of Nd, that is 0.125 moles of Nd; 30.2 g of copper nitrate, that is 0.125 moles of Cu; 10.62 g of sodium nitrate, that is 0.125 moles of Na; 75 g of a sol containing 40% of silica, that is 0.5 moles of $SiO_2$ and 800 ml of demineralized water are added to a 2-l beaker.

The mixture is heated to 60° C. and the mixture is sprayed while kept at this temperature.

The powder obtained is calcined for 3 hours at 850° C. The unmilled product has an average diameter of 10 μm and has the following chromaticity coordinates:
L*=41.8
a*=12.1
b*=−32.3

EXAMPLE 8

This example illustrates the preparation of a silicate of formula $Ba_{0.5}La_{0.5}Cu_{0.5}Na_{0.5}Si_2O_6$. The procedure of Example 7 is followed, the reactants being introduced in stoichiometric quantity. The lanthanum is introduced in the form of nitrate.

The product obtained after calcining for 2 hours at 950° C. has an average diameter of 5 μm and the following chromaticity coordinates:
L*=58
a*=5.1
b*=−43

EXAMPLE 9

This example is intended to illustrate the suitability of the pigments according to the invention for coloring plastics.

20 g of a pigment as prepared in Example 3 are mixed in a rotating cube with 2 kg of a polypropylene of reference Eltex® P HV 001.

The mixture is then extruded at 180° C. by means of a ZSK 30 twin screw extruder (marketed by the Werner and Pfleiderer Company).

The granules obtained are then injection-moulded at 220° C. by means of an Arburg 350-90-220 D injection press with a 41-second cycle.

The mold is maintained at a temperature of 35° C.

A parallelepipedal test piece of twin thickness (2 mm and 4 mm) is thus obtained, which is 49 mm in width and 69 mm in length. This test piece has a uniform violet color.

The chromaticity coordinates of this test piece, measured on the thick part of the latter (4 mm) are then the following:
L*=29.6
a*=7.3
b*=−16.2

EXAMPLE 10

This example illustrates the use of the products of the invention in cosmetics for the preparation of a make-up crayon. The constituent components are employed in the following proportions:

| Constituents | % by weight |
|---|---|
| A | |
| Silbione Oil 70633 V30 | 40 |
| B | |
| Beeswax | 15 |
| Carnauba wax | 7 |
| Ozokerite | 7 |
| Paraffin wax | 20 |
| Vaseline oil | q.s. 100 |
| Cetyl alcohol | 1 |
| C | |
| Silicate BaCuSi$_2$O$_6$ (example 3) | q.s. |
| Titanium oxide | q.s. |

The components of mixture B are melted and homogenized at 80±2° C. and are then kept in a thermostated bath controlled at 60±2° C. The silicate and the titanium oxide are dispersed in the Silbione oil; this mixture is placed in the thermostated bath at 60±2° C. Mixture B is then added. After homogenizing, the whole is poured into a silicone-treated mold.

We claim:

1. Silicate based on alkaline earths and copper, represented by formulas MCuSi$_4$O$_{10}$ or MCuSi$_2$O$_6$, where M represents the alkaline earth, wherein said silicate comprises agglomerates with an average size of no greater than 20 μm, composed of monocrystalline or mainly monocrystalline grains, or aggregates which are composed of monocrystalline particles.

2. Silicate based on alkaline earths, titanium and copper, represented by MCuTiSi$_3$O$_9$, where M represents the alkaline earth, wherein said silicate comprises agglomerates with an average size of no greater than 20 μm, composed of monocrystalline or mainly monocrystalline grains, or aggregates which are composed of monocrystalline particles.

3. Silicate according to claim 1, wherein the grains or aggregates have an average size of between 1 and 3 μm.

4. Silicate according to claim 1, wherein the agglomerates comprise deagglomerated agglomerates having an average size no greater than 5 μm.

5. Silicate according to claim 1, wherein the alkaline earth is barium.

6. Silicate according to claim 1, wherein the alkaline earth is partially replaced with a rare earth.

7. Silicate according to claim 1, wherein the copper is partially replaced with an element selected from the group consisting of an alkali metal, zinc, nickel, cobalt and magnesium.

8. Silicate according to claim 1 which corresponds to the formula BaCuSi$_2$O$_6$ and presents the following chromatic co-ordinates:
L*>30; a*>15; b*<−30.

9. Silicate according to claim 1 which corresponds to the formula BaCuSi$_4$O$_{10}$ and presents the following chromatic co-ordinates:
L*>40; a*<0; b*<−30.

10. A blue or violet pigment which includes at least one silicate based on alkaline earths and copper, represented by formulas MCuSi$_4$O$_{10}$ or MCuSi$_2$O$_6$, where M represents the alkaline earth, wherein said silicate comprises agglomerates with an average size of no greater than 20 μm, composed of monocrystalline or mainly monocrystalline grains, or aggregates which are composed of monocrystalline particles.

11. Process for preparing a silicate based on alkaline earths and copper, represented by formulas MCuSi$_4$O$_{10}$ or MCuSi$_2$O$_6$, where M represents the alkaline earth, wherein said silicate comprises agglomerates with an average size of no greater than 20 μm, composed of monocrystalline or mainly monocrystalline grains, or aggregates which are composed of monocrystalline particles, comprising the following stages:

mixing silica sol or a silicate and optionally a titanium sol with salts of other elements;

drying the resulting mixture; and calcining the resulting product.

12. Process according to claim 11, wherein the mixture is dried by atomization.

13. Process according to claim 11, wherein the calcined product is de-agglomerated.

14. Process according to claim 11, wherein said salts comprise nitrates.

15. A method for coloring a product selected from the group consisting of plastic materials, paints, coatings, rubbers, ceramics, glazes, papers, inks, cosmetic products, dyes and stratified coatings, said method comprising adding a color changing amount of silicate to said product, said silicate being based on alkaline earths and copper, represented by formulas MCuSi$_4$O$_{10}$ or MCuSi$_2$O$_6$, where M represents the alkaline earth, wherein said silicate comprises agglomerates with an average size of no greater than 20 μm, composed of monocrystalline or mainly monocrystalline grains, or aggregates which are composed of monocrystalline particles.

16. The silicate according to claim 1, having the formula MCuSi$_4$O$_{10}$.

17. The silicate according to claim 1, having the formula MCuSi$_2$O$_6$.

18. The silicate according to claim 4, wherein the agglomerates comprise deagglomerated agglomerates having an average size no greater than 3 μm.

19. Silicate according to claim 1, represented by Ba$_{0.5}$La$_{0.5}$CU$_{0.5}$Na$_{0.5}$Si$_4$O$_{10}$.

20. Silicate according to claim 1, represented by Ba$_{0.75}$Ca$_{0.25}$CuSi$_2$O$_6$.

21. Silicate according to claim 1, represented by BaCu$_{0.5}$Zn$_{0.5}$Si$_2$O$_6$.

22. Silicate according to claim 1, represented by Ba$_{0.9}$Cu$_{0.1}$TiSi$_3$O$_9$.

23. Silicate according to claim 1, represented by Ba$_{0.5}$Nd$_{0.5}$CU$_{0.5}$Na$_{0.5}$Si$_2$O$_6$.

24. Silicate acccording to claim 1, represented by Ba$_{0.5}$La$_{0.5}$CU$_{0.5}$Na$_{0.5}$Si$_2$O$_6$.

25. Single phase blue or violet pigments comprising the silicate according to claim 1.

26. Silicate according to claim 1, which presents the following chromatic co-ordinates:
L*=25 to 80, a*=−15 to +35, b*=−5 to −55.

27. Silicate according to claim 1, wherein Cu is partially replaced with Na or Li.

* * * * *